United States Patent [19]

Smith

[11] 4,198,992
[45] Apr. 22, 1980

[54] SMOKER'S APPLIANCE

[76] Inventor: Philip E. Smith, 94 Proteus St., Groton, Conn. 06340

[21] Appl. No.: 893,879

[22] Filed: Apr. 6, 1978

[51] Int. Cl.² ............................................. A24F 47/00
[52] U.S. Cl. ................................. 131/171 R; 131/175
[58] Field of Search ............... 131/175 R, 171 R, 174, 131/170 R, 187; 46/9; 128/185, 201

[56] References Cited

U.S. PATENT DOCUMENTS

| | | | |
|---|---|---|---|
| 402,681 | 5/1889 | Lindeman | 131/171 R |
| 2,510,909 | 6/1950 | Schuelein | 131/171 R |
| 2,960,981 | 11/1960 | Robertson | 131/171 R |
| 3,528,435 | 9/1970 | Morrissey | 131/171 R |

*Primary Examiner*—Stephen C. Pellegrino
*Attorney, Agent, or Firm*—Albert W. Hilburger

[57] ABSTRACT

A smoker's appliance capable of producing aircooled smoke in a sanitary and ashless manner for the pleasure of the user. The appliance is generally shaped like a gun having a cylindrical body with a threaded head at one end. A tube extends through an aperture formed in a cap which is threadedly engageable with the head. With the cap tightened onto the body, the tube permits communication between the chamber and the surrounding air. A flexible bulb is attached to the body at a location near an end opposite the head. By the use of appropriate check valves, the bulb, when squeezed, forces air into the chamber within the body without permitting its escape. When a lighted cigarette is inserted into a free end of the tube within the chamber, operation of the bulb causes a unitary direction of air flow through the appliance which assures long life for the cigarette. Cigarette smoke thus passes through the cigarette itself and exits from the tube, being preferably directed into the mouth of the user. Ashes from the cigarette are retained within the body until it is desired to disassemble it for cleaning, which can be readily accomplished.

6 Claims, 3 Drawing Figures

U.S. Patent  Apr. 22, 1980  4,198,992
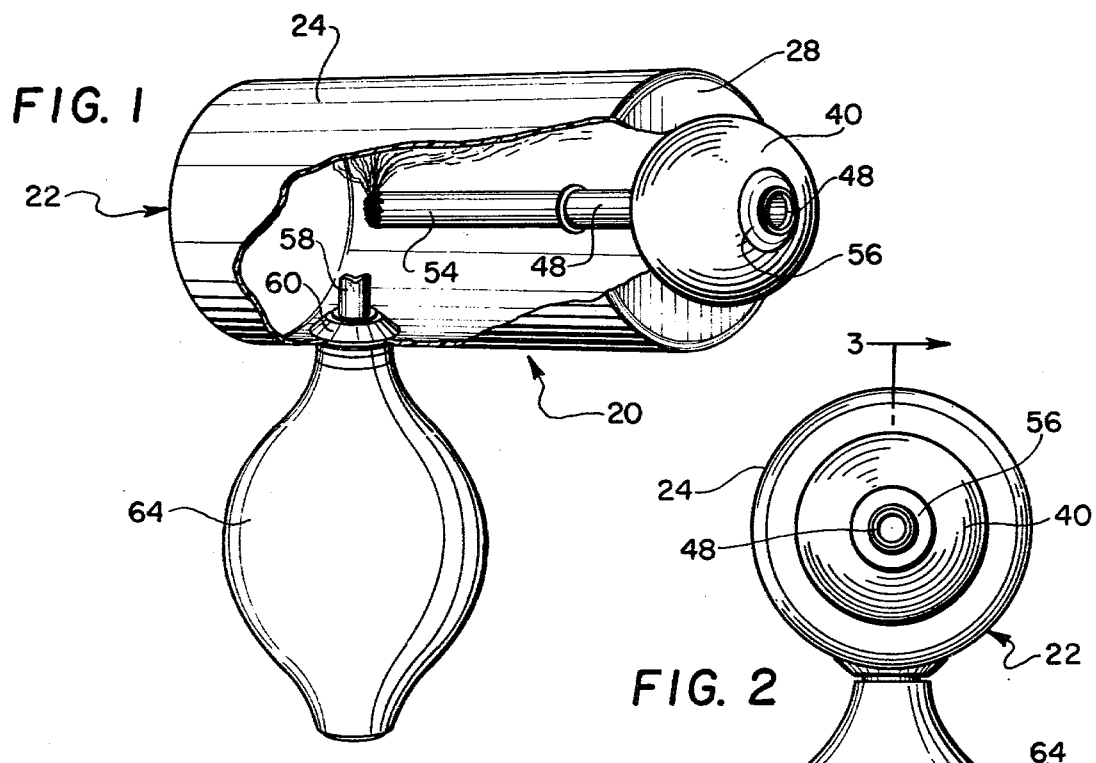
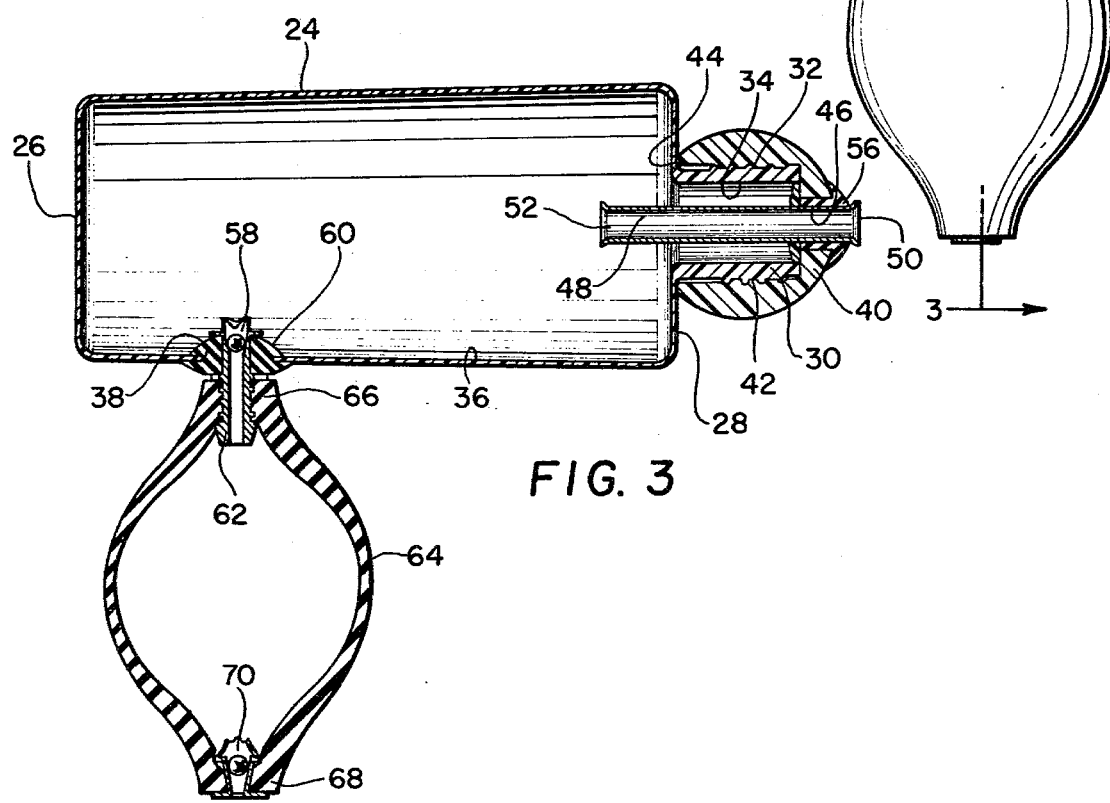

SMOKER'S APPLIANCE

BACKGROUND OF THE INVENTION

1. Field of the Invention

This invention relates generally to appliances for smokers and, particularly, to a new and improved variety of such appliances which serves to safely contain a smokeable article and to produce clean air cooled smoke in a sanitary and ashless manner for the pleasure of the user.

2. Description of the Prior Art

A variety of devices have been known to the prior art which serve to emit smoke or other vapors for pleasurable purposes. Representative of one such group are toys and, in one instance, smoke emitting toy locomotives as represented, for example, by the U.S. Pat. Nos. to Ives, 324,260 and to Goldfarb, 2,546,123. Another representative grouping of toys are those simulating jet propelled airplanes. Typical patents in this category are those to Brosseit, U.S. Pat. No. 2,409,471 and to Brosseit, U.S. Pat. No. 2,556,296. Also in the toy classification is the U.S. Pat. No. 2,788,607 which discloses a drum and associated smoke chamber so constructed that a beat on the drum causes a puff of smoke to emanate from the smoke generator in the shape of a smoke ring.

In a substantially different category of known devices, but more representative of the present invention, are the U.S. Pat. Nos. to Murai, 2,809,634, and to Schuelein, 2,510,909. In the former instance, an inhaling and sniffing pipe is disclosed which enables a user to inhale volatile liquids which produce, for example, fragrance of tobacco and tobacco smoke, as a substitute for smoking lighted tobacco. Quite different structurally from Murai, the Schuelein patent discloses a device for holding a smokeable article, such as a cigar or cigarette, so that a user can obtain the satisfaction of the aroma of tobacco and of seeing smoke without actually bringing the smokeable article to the user's mouth or requiring him to inhale the tobacco fumes. A chief drawback of the latter patent is that an ignited cigar or cigarette is not enclosed within a structure and is therefore able to completely drop from the holder and away from the person of the user. Additionally, ashes or lighted particles may drop off and ignite clothing, furniture, rugs, and the like, nor is any structure disclosed for directing the smoke or aroma from the cigar or cigarette in a particular direction.

While another representative patent, U.S. Pat. No. 2,960,981 does provide a container enclosing a smokeable article, it is of relatively complex construction of a magnitude not sufficiently larger than the smokeable article to assure dissipation of the heat generated. Additionally, unlike the present invention, the U.S. Pat. No. 2,960,981 causes increased burning not only upon compression of the bulb but also upon release and return of the bulb to its original shape.

SUMMARY OF THE INVENTION

The present invention was conceived with knowledge of these prior art devices, the purpose being to provide an improved smoker's appliance capable of producing air cooled smoke in a sanitary and ashless manner for the pleasure of the user. To this end, the invention herein disclosed is generally shaped in the form of a gun for ease of operation and has a cylindrical body with a threaded head at one end. A flexible bulb is attached to the body at a location near an end opposite that of the head. By the use of appropriate check valves on the body and on the bulb, respectively, when the bulb is squeezed air is forced into a chamber within the body without permitting its escape. A tube extends through an aperture formed in a cap which is threadly engageable with the head. With the cap tightened onto the body, the tube permits communication between the chamber and ambient air. When a cigarette is inserted into a free end of the tube, then lighted and inserted into the chamber and the cap tightened onto the body, operation of the bulb causes a unitary direction of air flow through the chamber, thus assuring longevity of the cigarette. Smoke from the cigarette thus passes through the cigarette itself and exits from the tube, being preferably directed into the mouth of the user. Ashes from the cigarette are retained within the body until it is desired to disassemble it from cleaning. The structure of the appliance disclosed permits its rapid disassembly and reassembly for cleaning, for replacement of components, or for any other appropriate purpose.

Among the features of the present invention are its simplified construction whereby it requires a minimum of parts and utilizes existing materials. Although the appliance can be readily assembled and disassembled, it maintains an airtight construction by the use of appropriate seals.

A primary feature of the invention presides in its double valve construction which assures unitary direction of flow through the chamber resulting in longer life to the cigarette. Thus, the invention is economical in operation.

Since the invention disclosed is shaped like a gun, it can be easily handled by the user. In addition, the ignited cigarette or other smokeable article is normally completely contained within the structure of the invention so that it cannot cause damage to anyone or anything coming in close proximity to the appliance. Furthermore, the air which is introduced into the body keeps the body cool to the touch when the cigarette is in a burning condition and the structure enclosing the cigarette also serves to retain spent ashes for later disposal. Also, the appliance is sanitary and provides a maximum of pleasure to the user which results from the construction which enables smoke from the burning cigarette to be directed into the user's mouth without requiring the user's mouth to touch the appliance.

Other and further features of the invention will become apparent from the following description taken in conjunction with the following drawings. It is to be understood that both the foregoing general description and the following detailed description are exemplary and explanatory but are not restrictive of the invention. The accompanying drawings, which are incorporated in and constitute a part of this invention, illustrate one embodiment of the invention, and together with the description, serve to explain the principles of the invention.

BRIEF DESCRIPTION OF THE DRAWINGS

In the drawings:

FIG. 1 is a perspective view of the invention, partially cut away and in section to illustrate its interior;

FIG. 2 is a front elevation view of the invention illustrated in FIG. 1; and

FIG. 3 is a cross section view taken generally along line 3—3 in FIG. 2.

DESCRIPTION OF THE PREFERRED EMBODIMENTS

Refer now to the drawings and initially to FIGS. 1 and 2 which generally illustrate a smoker's appliance 20 which is the subject of the present invention.

In accordance with the invention, the smoker's appliance 20 includes a cylindrical hollow body defining a substantially airtight chamber including a head member of reduced diameter integral therewith and extending outwardly from one end thereof, said head member being threadedly externally and having a central bore extending therethrough, the longitudinal axis of the bore being substantially coincident with the longitudinal axis of the chamber, said body having an opening through its curved outer sidewall distant from said head member. As embodied herein, a cylindrical hollow body generally indicated by reference numeral 22 has a curved outer sidewall 24, which terminates at a substantially flat end wall 26. At the end of the body 22 opposite from the end wall 26 is a shoulder 28 from which extends outwardly a head member 30 (see FIG. 3). The head member 30 is preferably integral with the remainder of the body 22 and is threaded as at 32 on its outer surface. A bore 34 extends through the head member 30 and is coextensive of the head member. A longitudinal axis of the bore 32 is substantially coincident with the longitudinal axis of a chamber 36 within the body 22 as defined by the sidewall 24, the end wall 26 and by the shoulder 28. At a location distant from the head member 30, the body 22 is formed with an opening 38 (FIG. 3) which extends through the outer sidewall 24.

In accordance with the invention, a cap is threadedly received on said head member and includes a rim engageable with said body when said cap is screwed to its limit on said head, said cap having an aperture therethrough with an axis substantially coincident with the longitudinal axes of the bore and the chamber. As embodied herein, with particular reference to FIG. 3, a cap 40 has threads 42 which mate with the threads 32 of the head member 30. Additionally, the cap 40 includes a rim 44 at one end which is engageable with the shoulder 28 of the body 22 when the cap is screwed to its limit on the head. The cap 40 is formed with an aperture 46 which extends through the cap and which has an axis substantially coincident with the longitudinal axis of the bore 34 an of the chamber 36.

In accordance with the invention, a tube extends through the aperture extending from an outer end at a location outside of the chamber to an inner end at a location within the chamber when the cap is threadedly engaged with said head member, said tube adapted to fittingly receive and hold a smokeable article at its inner end. As embodied herein, with continuing reference to FIG. 3, a tube 48 is seen to extend through the aperture 46 from an outer end 50 which is located outside of the chamber 36 and indeed beyond the cap 40 and all other structure of the appliance 20, to an inner end 52 at a location within the chamber 36 when the cap 40 is threadedly engaged with the head member 30 as illustrated in FIG. 3. The tube 48 may be flared at both ends and, at its inner end 52, is adapted to fittingly receive and hold a smokeable article 54 (see FIG. 1) such as a cigar or cigarette. As best seen in FIG. 3, a first resilient grommet 56 is fittingly received within the aperture 46 and itself fittingly receives the tube 48, enabling the tube to assume a position, as previously described, coaxial with the cap 40 and with the head member 30.

In accordance with the invention, the appliance 20 further includes first valve means fittingly mounted to said body at the opening therethrough and including a stem extending outwardly from said body, said first valve means adapted to permit the entry of air into the chamber while preventing the escape of air therefrom; and a second resilient grommet fittingly mounting said first valve means to said body. As embodied herein, and with reference once again to FIG. 3, a check valve 58 is fittingly mounted to the sidewall 24 of the body 22 by means of a second resilient grommet 60 which is itself fittingly received within the opening 38. The valve 58 is provided with an integral stem 62 which extends generally radially outwardly from the sidewall 24 of the body 22. The valve 58 may be any of a variety of suitable check valves which function to permit the entry of air into the chamber 36 while preventing the escape of air from the chamber.

In accordance with the invention, the appliance 20 further includes a flexible bulb apertured at one end for fitting reception on said stem and including second valve means distant from said first valve means adapted to permit entry of ambient air into the interior of said bulb while preventing the escape of air therefrom. As embodied herein, with particular attention to FIGS. 1 and 3, a flexible bulb 64, which may be composed of a soft rubber like substance or other suitable flexible material, is apertured at an end 66 for fitting reception on the stem 62 of the valve 58. Integral with the bulb 64 at an end 68 opposite the end 66 is a second check valve 70 which is functionally similar to the valve 58 in that it is adapted to permit entry of ambient air into the interior of the bulb 64 while preventing the escape of air from the bulb.

Now that the structure of the smoker's appliance has been disclosed, its operation will be described. A user of the appliance 20 inserts a smokeable article such as a cigar or cigarette 54 into the end 52 of the tube 48. The free end of the smokeable article is thereupon lighted by means of a match or other suitable igniting device, and the cap 40 is screwed onto the head member 30 until the rim 44 firmly engages the shoulder 28 of the body 22.

Thereupon, the user preferably applies slow steady pressure to the bulb 64 by squeezing it until it is fully compressed, then releasing it and continuing the process in a regular and continuous fashion. In this manner, air drawn into the interior of the bulb 64 is thereupon forced through the valve 58 into the chamber 36. The smokeable article 54 is thereby provided with the oxygen needed to continue its combustion and the pressure thus created within the chamber 36 causes smoke from the article 54 to pass along its length, through the tube 48, and out the flared outer end 50. The construction assures that a directed stream of smoke will emanate through the end 50 of the tube 48 and a user can take enjoyment from the smoke by directing the flow of smoke out of the outer end 50 into his mouth. Of course, it will be appreciated that it is not necessary and, in fact, would be unde-irable and unsanitary, for the user to place his mouth on the cap 40.

Continuing with the cycle of operation, when the bulb 64 has been squeezed, then released, the valve 70 will operate to permit ambient air to refill the bulb 64, but once such air is in the bulb 64, it cannot thereafter escape from the end 68. Continued operation of the bulb 64 assures the continual presence of cool air within the chamber 36. In this manner, the body 22 remains cool to the touch and capable of being held without causing injury to the user even when a smokeable article 54 has been lighted for long periods of time. The large relative size of the chamber 36 with respect to the smokeable article 54 also aids in keeping the body 22 cool to the touch.

Furthermore, the construction utilizing the two check valves, 58 and 70, respectively, assures that only one direction of air flow through the chamber will result. Specifically, the direction of air flow through the chamber 36 is always such that air flows from the lighted end of the smokeable article 54, then along its length, and eventually out the end 50 of the tube 48. The valve 58 prevents the flow of air through the tube 48 and into the chamber 36 when the tube 64 is in the process of refilling with ambient air. In this manner, the smokeable article 54 will be caused to burn in a steady, but not excessive manner so that the user will obtain a maximum benefit at a minimum of waste and expense.

As the smokeable article 54 is burned, its ashes drop to the bottom of the chamber 36 and remain contained until a later time. When the article 54 has been substantially consumed, the user can unscrew the cap 40, dispose of the butt remaining, and empty the ashes through the head member 30. Additionally, it will be appreciated that all of the remaining components of the appliance 20 can be readily disassembled for cleaning and readily reassembled when it is again desired to return the appliance to service.

The invention in its broader aspects is not limited to the specific details shown and described; departures may be made from such details without departing from the principles of the invention and without sacrificing its chief advantages.

What is claimed is:

1. A smoker's appliance comprising:
   a hollow body defining a substantially airtight chamber, having a first opening adjacent one end thereof;
   a closure member fittingly engageable with said body at said one end for selectively sealing the first opening and including a tubular member extending therethrough from a location outside of the chamber to a location within the chamber when said closure member is engaged with said body, said tubular member adapted to fittingly receive and hold one end of a smokeable article within the chamber;
   first valve means mounted to said body at a location distant from said closure member adapted to permit the entry of ambient air into the chamber while preventing the escape of air from the chamber;
   pump means mounted on said body at said first valve means for selectively pumping air into the chamber; and
   second valve means integral with said pump means distant from said first valve means adapted to permit the entry of ambient air into the interior of said bulb while preventing the escape of air therefrom.

2. A smoker's appliance as set forth in claim 1 wherein said hollow body includes a threaded head member at one end defining the opening into the chamber and wherein said closure member is a cap threadedly engageable with said head member.

3. A smoker's appliance as set forth in claim 2 wherein said cap has an aperture therethrough, said tubular member extending through the aperture; a resilient seal fittingly mounting said tubular member to the closure member within the aperture; and said tubular member being flared at both ends.

4. A smoker's appliance as set forth in claim 3 wherein said body has a second opening distant from the first opening and including a resilient seal fittingly received within the second opening and having a bore extending therethrough, and wherein said first valve is fittingly received within the bore of said resilient seal and extends outwardly from said body, and wherein said pump means includes a flexible bulb having one end fittingly received on said first valve means.

5. A smoker's appliance comprising:
   a cylindrical hollow body defining a substantially airtight chamber including a head member of reduced diameter integral therewith and extending outwardly from one end thereof, said head member being threaded externally and having a central bore extending therethrough, the longitudinal axis of the bore being substantially coincident with the longitudinal axis of the chamber, said body having an opening through its curved outer sidewall distant from said head member;
   a cap threadedly received on said head member and including a rim engageable with said body when said cap is screwed to its limit on said head, said cap having an aperture therethrough with an axis substantially coincident with the longitudinal axes of the bore and the chamber;
   a tube extending through the aperture extending from an outer end at a location outside of the chamber to an inner end at a location within the chamber when the cap is threadedly engaged with said head member, said tube adapted to fittingly receive and hold a smokeable article at its inner end;
   a first resilient grommet fittingly mounting said tube to said cap;
   first valve means fittingly mounted to said body at the opening therethrough and including a stem extending outwardly from said body, said first valve means adapted to permit the entry of air into the chamber while preventing the escape of air therefrom;
   a second resilient grommet fittingly mounting said first valve means to said body; and
   a flexible bulb apertured at one end for fitting reception on said stem and including second valve means distant from said first valve means adapted to permit entry of ambient air into the interior of said bulb while preventing the escape of air therefrom.

6. A smoker's appliance as set forth in claim 5 wherein said bulb is composed of a rubber like substance and wherein said tube is flared at both ends.

* * * * *